United States Patent [19]

Baumberg

[11] Patent Number: 4,706,777

[45] Date of Patent: Nov. 17, 1987

[54] STETHOSCOPE

[76] Inventor: Iosif Baumberg, 54 Bay 29 St., Brookyln, N.Y. 11510

[21] Appl. No.: 832,724

[22] Filed: Feb. 25, 1986

[51] Int. Cl.$^4$ ............................................... A61B 7/02
[52] U.S. Cl. .................................... 181/131; 181/137
[58] Field of Search ................................ 181/131, 137

[56] References Cited

U.S. PATENT DOCUMENTS

| | | | |
|---|---|---|---|
| 1,671,936 | 5/1928 | Rieger | 181/137 |
| 1,708,398 | 4/1929 | Pilling | 181/131 |
| 1,853,951 | 4/1932 | Zala | 181/137 |
| 2,209,164 | 7/1940 | Kerr | 181/137 |
| 3,144,091 | 8/1964 | Bodenger | 181/137 |

Primary Examiner—Benjamin R. Fuller
Attorney, Agent, or Firm—Ilya Zborovsky

[57] ABSTRACT

A stethoscope has two sound transmitting tubular elements with the ends insertable into ears of an examining person, and two sound receiving end pieces applicable onto a body at a distance from one another and communicating with the sound transmitting tubular elements to provide stereo information about sounds inside the body. The stethoscope can be adjusted to reception of mono sounds, and also for providing different sound transmission through the sound transmitting tubular elements.

6 Claims, 5 Drawing Figures

STETHOSCOPE

BACKGROUND OF THE INVENTION

The present invention relates to a stethoscope.

Known stethoscopes include a single sound receiving end piece which is connected with two tubular sound transmitting members. The opposite end of the latter are insertable into right and left ears of a person who conducts the respective examination. The disadvantages of the known stethoscopes is that it is impossible with its use to receive a spacial information from a source of sound to be examined.

SUMMARY OF THE INVENTION

Accordingly, it is an object of the present invention to provide a stethoscope which allows a physician or another examining person to obtain a spacial information about processes with take place in a human's organism etc.

In keeping with these objects and with others which will become apparent hereinafter, one feature of the present invention resides, briefly stated, in a stethoscope which has two sound receiving end pieces connected with sound transmitting tubular members, so that an examining person who uses the stethoscope receives a spacial or stereo sound information.

In accordance with another especially advantageous feature of the present invention, the stethoscope is provided with means for adjusting sound transmission through the tubular sound transmitting members so that the sound transmission through one of them is different from the sound transmission through the other. This is important when a physician has different hearing capability in his ears, or for performing special examinations as will be explained hereinbelow.

The novel features of the present invention are set forth in particular in the appended claims. The invention itself, however, will be best understood from the following description of preferred embodiments, which is accompanied by the following drawings.

DESCRIPTION OF PREFERRED EMBODIMENTS

Figure 1:
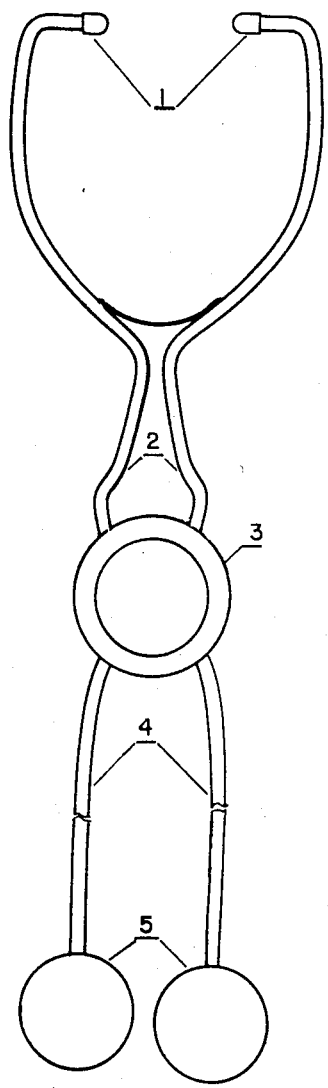
FIG. 1 is a view showing a stethoscope in accordance with the present invention.

A stethoscope in accordance with the present invention has two plugs 1 which are insertable into ears of an examining person, two tubular sound transmitting members 2 connected with the plugs 1, and two sound receiving end pieces 5 which are connected with the tubular sound transmitting members 2 through two tubular extensions 4 and a valve 3.

The valve 3 has a housing with two openings 7 and 8 which are permanently connected with the tubular members 2 and two further openings 9 and 10 which are permanently connected with the tubular extensions 4. A valve body 6 are turnable in the valve housing and has passages which are formed as shown in the drawing. More particularly, the valve body has three substantially parallel passages, and one transverse passage which connects two parallel passages with one another. In the position shown in FIG. 2, the left sound receiving end piece 5 directly communicates with the left plug 1, and the right sound receiving end piece 5 directly communicates with the right plug 1, through the openings 9,7 and 10,8 in the valve 3, respectively.

Figure 3:
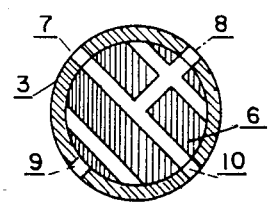

In the position shown in FIG. 3 only the right sound receiving end piece 5 communicates with both tubular sound transmitting member 2 and two plugs 1 through the openings 10,7 and 10,8 of the valve 3, respectively.

Figure 2:
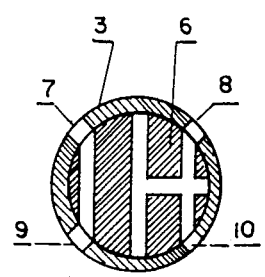
FIGS. 2 and 3 are views showing a valve of the inventive stethoscope in two different positions.

When the stethoscope is used in the position shown in FIG. 2, the sound receiving end pieces are applied onto a human body at a certain distance from one another and a physician receives stereo sounds. First of all, a physician can determine the location and depth of a sound source, thus obtaining a spacial sound information. Moreover, if a physician examines symmetrical parts of the body, for example pulse beats on left and right arms of a patient, he hears an imaginary sound source and the location of the latter gives him an information about the time of filling with blood of identical blood vessels of the right part and the left part of the body and therefore their resistance to blood flow, or in other words their permeability.

When the stethoscope is used in the position shown in FIG. 3, a physician receives mono sounds, for example for routine determination of blood pressure or pulse of a patient.

Figure 4:
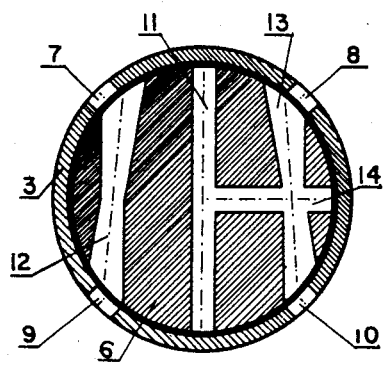
FIG. 4 shows the inventive valve in accordance with another embodiment of the invention.

In the embodiment shown in FIG. 4, passages 12 and 13 are inclined relative to one another by a small angle. Both opposite ends of each of the passages 12 and 13 expandsd outwardly towards the valve housing. A central passage 11 is located between the passages 12 and 13. The passage 14 extends transversely and communicates with the passages 11 and 14, and also opens outwardly.

Similarly to the embodiment of FIGS. 2 and 3 the valve body of the valve shown in FIG. 4 can be turned so that it allows mono sound reception or stereo sound reception. In contrast to the embodiment of FIGS. 2 and 3, the valve shown in FIG. 4 also allows adjustment of sound transmission from the end pieces 5 to the plugs 1 through different tubular sound transmitting members 2. If the valve body 6 is turned from the position shown in FIG. 4 counterclockwise by a small angle, the cross section of the openings 9 and 7 remains the same, while the material of the valve body 6 obstructs a part of the openings 10 and 8. Therefore the sound transmission to the right plug 1 will be lower than to the left plug. This is advisable when hearing of the left ear of a physician is higher than in the right ear. Turning of the valve body 6 in clockwise direction reduces the sound transmission to the left plug.

The tubular extensions 4 are connected detachably with the valve 6, for example by a thread of the upper end of the tubular extension and the threaded openings in the valve. Thereby, in the mono sound examination the one tubular extension 4 with one sound receiving end piece 5 can be unscrewed and detached.

The invention is not limited to the details shown since various modifications and structural changes are possible, without departing in any way from the spirit of the present invention.

Figure 5:
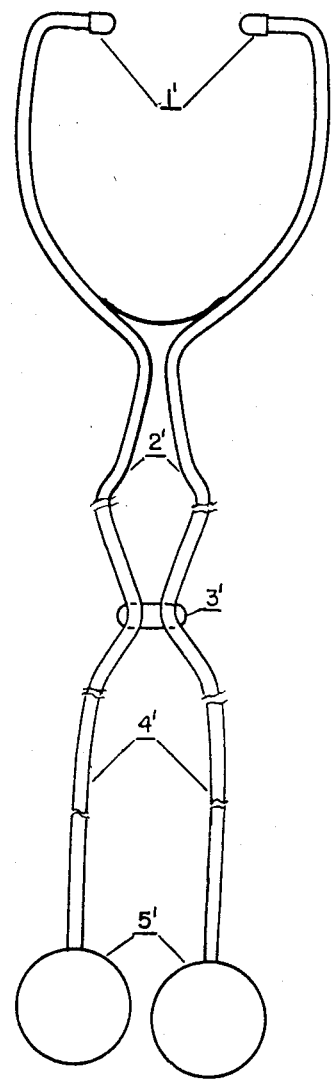
FIG. 5 is a view showing the stethoscope in accordance with still a further embodiment.

FIG. 5 shows a different embodiment of the invention. In the stethoscope of this embodiment the plugs 1' and permanently connected through the tubular sound transmitting members 2', the tubular extensions 4' with the sound receiving end pieces 5' respectively, individually and separately from one another so that the stethoscope always operates in stereo sound receiving mode.

The invention is not limited to the details shown since various modifications and structural changes are possible without departing in any way from the spirit of the present invention.

What is desired to be protected by Letters Patent is set forth in particular in the appended claims.

I claim:

1. A stethoscope, comprising
   two sound transmitting tubular elements each having two opposite ends formed so that one end of one sound transmitting tubular element is insertable into one ear of an examining person and one end of the other sound transmitting tubular element is insertable into the other ear of the examining person;
   two sound receiving end pieces each applicable to the body of a person to be examined at a distance from one another and each connected with the other end of a respective one of said sound transmitting tubular elements so that one of said sound receiving end pieces is connected with one of said sound transmitting tubular elements but is not connected with the other of said sound transmitting tubular elements while the other of said sound receiving end pieces is connected with the other of said sound transmitting tubular elements but is not connected with said one sound transmitting tubular element and therefore one sound channel is formed by said one sound receiving end piece and said one sound transmitting tubular element and another sound channel is formed by said other sound receiving piece and said other sound transmitting tubular element, and said channels do not communicate with one another so that when said sound receiving end pieces are applied to the body at a distance from one another, sound from the body are transmitted from said sound receiving end pieces through said sound transmitting tubular elements through said one and other noncommunicating sound channels into the ear of the examining person and therefore the latter receives stereo sound information; and means for connecting said sound receiving end pieces with said sound transmitting tubular elements and including a valve member moveable between a stereo position in which each of said sound receiving end pieces is connected with a respective one of said sound transmitting tubular elements and the examining person receives the stereo sound information, and a mono position in which only one of said sound receiving end pieces is connected with both said sound transmitting tubular elements and therefore the examining person receives mono sound information.

2. A stethoscope as defined in claim 1, wherein each of said sound receiving end pieces is provided with a tubular outlet connected with a respective one of said sound transmitting tubular elements, said valve being arranged between said tubular outlets of said sound receiving end pieces and said sound transmitting tubular elements.

3. A stethoscope as defined in claim 1; and further comprising means for adjusting sound transmission through said sound transmitting tubular elements so that in one of said sound transmitting tubular elements the sound transmission is higher than in the other sound transmitting tubular element.

4. A stethoscope as defined in claim 3, wherein said adjusting means is formed as means for steplessly adjusting the sound transmission through said sound transmitting tubular elements.

5. A stethoscope as defined in claim 3, wherein said adjusting means includes said valve connecting said sound receiving end pieces with said sound transmitting tubular elements and movable between a pluralilty of positions including at least one first position in which the sound transmission through both said sound transmitting tubular elements is the same, and at least one second position in which said transmission through said sound transmitting tubular elements is different from one another.

6. A stethoscope as defined in claim 5, wherein said valve includes a housing having two pairs of openings such that the openings of one pair permanently communicate with said sound receiving and pieces while the openings of the other pair pemanently communicate with said sound transmitting tubular elements, an a valve body movable in said housing and having at least two channels formed so that each of said channels has one end for communicating with one opening of said one pair and with one opening of the other pair, said channels having inclined axes, and each of said ends of said channels expanding outwardly towards said openings.

* * * * *